United States Patent [19]

Updike et al.

[11] 4,329,427

[45] May 11, 1982

[54] FERMENTATIVE PREPARATION OF L-ISOLEUCINE

[75] Inventors: Mark H. Updike, Baltimore; Gary J. Calton, Elkridge, both of Md.

[73] Assignee: W. R. Grace & Co., New York, N.Y.

[21] Appl. No.: 194,113

[22] Filed: Oct. 6, 1980

[51] Int. Cl.³ .............................................. C12P 13/06
[52] U.S. Cl. .................................... 435/116; 435/840
[58] Field of Search ............................... 435/116, 840

[56] References Cited

U.S. PATENT DOCUMENTS 4,237,228 12/1980 Zhdanova et al. .................. 435/116

Primary Examiner—Lionel M. Shapiro
Attorney, Agent, or Firm—Philip M. Pippenger

[57] ABSTRACT

L-isoleucine is prepared by cultivation of an analogue-resistant mutant of *Brevibacterium thiogenitalis* in an aqueous nutrient medium under aerobic conditions in the presence of from 0.001 to 15 w/v percent of a post-threonine precursor for L-isoleucine. The cultivation is preferably carried out at about 30° C. and at a pH of 5 to 9. L-isoleucine is recovered from the fermentation broth.

9 Claims, No Drawings

FERMENTATIVE PREPARATION OF L-ISOLEUCINE

BACKGROUND OF THE INVENTION

Production of L-isoleucine, L-valine and other amino acids via fermentation has been the subject of considerable research. Numerous genera of microorganisms have been employed along with various analogues of L-isoleucine, threonine, valine, etc. From U.S. Pat. No. 3,893,888 it is known that L-valine can be produced from mutant strains of Brevibacterium resistant to α-amino-β-hydroxy valeric acid (AHV). The biosynthetic pathways in Brevibacterium for production of L-isoleucine using ethionine and AHV as antagonists have also been studied. See:

Ikeda, S., I. Fujita and Y. Hirose. (1976). Culture conditions of L-isoleucine fermentation from acetic acid. *Agr. Biol. Chem.*, 40(3), 517–522.

Ikeda, S., I. Fugita and F. Yoshinaga. (1976).Screening of L-isoleucine producers among ethionine resistant mutants of L-threonine producing bacteria. *Agr. Biol. Chem.*, 40(3), 511–516.

Shiio, Isamu, A. Sasaki, S. Nakamori and K. Sano. (1973). Production of L-isoleucine by AHV resistant mutants of Brevibacterium flavum. *Agr. Biol. Chem.*, 37(9), 2053–2061.

Several general articles on biosynthetic pathways for producing L-isoleucine as well as other amino acids have also been published. See:

Szentirmai, A. and I Horvath. (1976). Regulation of branched-chain amino acid biosynthesis. *Acta Microbiol. Acad. Sci. Hung.*, 23, 137–149.

Umbarger, H. E. (1974). The elements involved in the multivalent regulation of the isoleucine and valine biosynthetic enzymes of the enterobacteriaceae. *Proceedings of the 1st. Intersectional Congress of IAMS*, 1, Tokyo.

Umbarger, H. E. (1973). Genetic and physiological regulation of isoleucine, valine and leucine formation in the *Enterobacteriaceae*. From "Genetics of Industrial Microorganisms".

The biosynthetic pathway for production of L-isoleucine in Serratia marcescens has also been extensively studied using various antagonists such as isoleucine hydroxamate, and α-aminobutyric acid. Pathways for L-isoleucine production in E.coli have also been studied using antagonists such as thiaisoleucine. Alpha-aminobutyric acid has also been employed as an antagonist in studying L-isoleucine production in Bifidobacterium. L-isoleucine production has also been studied in microorganisms of the genus Pseudomonas, Salmonella (using $5^1,5^1,5^1$-trifluoroleucine as an antagonist) and in Streptomyces rimosus.

In addition to those described above, numerous processes have been patented for the production of L-isoleucine. See U.S. Pat. No. 3,058,888 (Pseudomonas strains requiring α-aminobutyric acid); U.S. Pat. No. 3,231,478 (Brevibacterium requiring threonine); U.S. Pat. No. 3,262,861 (Brevibacterium requiring α-aminobutyric acid); U.S. Pat. No. 3,532,600 (Arthrobacter citreus requiring α-aminobutyric acid); U.S. Pat. No. 3,671,396 (Brevibacterium requiring α-aminobutyric acid, α-hydroxybutyric acid or threonine) and U.S. Pat. No. 3,841,968 (Serratia marcescens requiring L-threonine, L-homoserine or L-aspartic acid with resistance to isoleucine hydroxamate and/or α-aminobutyric acid).

DESCRIPTION OF THE INVENTION

The invention is a process for preparing L-isoleucine which comprises cultivating under aerobic conditions a mutant strain of Brevibacterium thiogenitalis resistant to an analogue of L-isoleucine. Cultivation, i.e., fermentation, is carried out in the presence of a post-threonine biosynthetic precursor of L-isoleucine to accumulate L-isoleucine in the fermentation broth.

Wild strains of Brevibacterium thiogenitalis (e.g., ATCC 19240) selected for mutation are characterized by overproduction of glutamic acid. The mutant strains useful in the invention do not require precursors for growth but do require the precursor for production of L-isoleucine. In the absence of the precursor, production is shifted to L-valine. The biosynthetic pathway whereby microorganisms produce L-isoleucine is generally known. See for example Umbarger, "Amino Acid Biosynthesis and Its Regulation", *Ann. Rev. Biochem.* 1978. 47:533–606. As stated in this reference, the synthesis is believed to proceed through the following stages: threonine; α-ketobutyrate; α-aceto-β-hydroxybutyrate; α,β-dihydroxy-β-methylvalerate; α-keto-β-methylvalerate; L-isoleucine. The term "post-threonine precursors" is intended to include precursors of L-isoleucine subsequent to threonine and compounds similar thereto, e.g., α-hydroxy butyric acid and α-amino-n-butyric acid. Generally the precursors can be employed in the form of acids or water soluble salts thereof, e.g., alkali metal salts with the sodium salt being preferred. The mutants described above are characterized in that the threonine conversion to α-ketobutyrate is hindered, i.e., to produce L-isoleucine rather than L-valine, the post-threonine L-isoleucine precursor must be present.

Certain analogues of the naturally occurring amino acids are suitable for isolating the mutant strains of this invention. These analogues are are toxic to strains which do not overproduce L-isoleucine. Such analogues include α-amino-β-hydroxyvaleric acid; methylglycine; gamma-dehydroisoleucine; 3-cyclopentine-1-glycine; 2-cyclopentene-1-glycine; o-methylthreonine; and β-hydroxyleucine.

The isoleucine analogue resistant mutant may be obtained by ultraviolet irradiation of a wild type strain of Brevibacterium thiogenitalis or by treating the wild strain with a mutagen, e.g., ethyl methane sulfonate, N-methyl-N$_1$-nitro-N-nitrosoguanidine, etc. Thereafter the strain can be cultured in the presence of the analogue to isolate the colonies which overproduce L-isoleucine. For example the unrelated strain can be cultured at 30° C. for 2 to 7 days on agar plates of the following composition: gelatin hydrolysate peptone, 5.0 g/l; beef extractives, 3.0 g/l; agar, 15 g/l; 2 hydroxy-β-valeric acid sodium salt, 25 g/l.

A viable culture of an L-isoleucine-producing mutant strain of Brevibacterium thiogenitalis resistant to α-amino-β-hydroxyvaleric acid has been deposited with the American Type Culture Collction, 12301 Park Lawn Drive, Rockville, Maryland 20852, under No. ATCC 31723.

Fermentation of the isolated mutant strains of Brevibacterium thiogenitalis can be accomplished by shaking cultivation or submerged fermentation under aerobic conditions. The fermentation is carried out at 20° to 45° C. and at a pH of 5 to 9. Calcium carbonate and ammonia may be employed for adjustment of the pH of the medium. The fermentation medium contains a source of carbon, a source of nitrogen and other elements. Suitable sources of carbon for the fermentation include fermentable sugars, protein hydrolysates and proteins. Examples of suitable sources of nitrogen are urea, ammonium salts of organic acids (e.g., ammonium acetate and ammonium oxalate) and ammonium salts of inorganic acids (e.g., ammonium sulfate, ammonium nitrate or ammonium chloride). The amounts of the carbon and nitrogen sources in the medium are from 0.001 to 20 w/v percent. Also, organic nutrients (e.g., corn steep liquor, peptone, yeast extracts) and/or inorganic elements (e.g., potassium phosphate, magnesium sulfate, vitamins such as biotin and thiamine, and amino acids, e.g., isoleucine and valine) may be added to the medium. The amount of the L-isoleucine precursor is from 0.001 to 20 w/v percent of the medium. The fermentation is accomplished in 16 to 176 hours, and L-isoleucine is accumulated in the fermentation broth.

After the fermentation is completed, i.e., from 0.1 to 6 w/v percent of L-isoleucine is accumulated in the broth, cells and other solid culture components are removed from the fermentation broth by conventional procedures such as heating followed by filtration or centrifugation. Known procedures may be employed in the recovery and/or purification of L-isoleucine from the filtrate or the supernatant solution. For instance, the filtered fermentation broth is treated with a strong cation exchange resin. Then the resin is eluted with a dilute alkaline solution such as aqueous ammonia. The eluates containing L-isoleucine are combined and concentrated. An alkanol such as methanol or ethanol is added to the concentrated solution. The precipitated crystals can be recrystallized from an aqueous alkanol such as aqueous methanol and aqueous ethanol to yield pure crystals of L-isoleucine.

The following examples illustrate preferred embodiments of the invention.

EXAMPLE 1

Test tubes containing 10 ml each of 0.1 M phosphate buffer (pH 7.0) were innoculated with cultures of Brevibacterium thiogenitalis (ATCC 19240). The resulting suspension was shaken vigorously and 9 ml from each tube was transferred to a sterile centrifuge tube to which was added 1 ml of aqueous ethyl methane sulfonate (EMS) to provide an EMS concentration of 0.06 M in the suspension. The suspensions were incubated at 30° C. for 18 hours and spun down to isolate the cells which were resuspended in deionizied water and centrifuged again. This procedure was repeated several times to remove EMS.

EXAMPLE 2

Mutated microorganisms from Example 1 were plated onto gradient plates consisting of two layers. The lower layer included α-amino-β-hydroxy valeric acid (AHV), 25 g/l, and had the following composition: gelatin hydrolysate peptone, 5.0 g/l; beef extractives, 3.0 g/l; agar, 15 g/l. The upper layer had a similar composition but did not contain AHV. Representative colonies were selected from the "low-growth" side of the plate and were used to innoculate the following media: gelatin hydrolysate peptone, 5.0 g/l; beef extractives, 3.0 g/l; and agar, 15 g/l.

Fermentation was carried out for 4 days at a temperature of 30° C. in 250 ml Erlenmeyer flasks rotated at 300 rpm. The media contained glucose, 100 g/l; $KH_2PO_4$, 3 g/l; $MgSO_4.7H_2O$, 14 g/l; $FeSO_4.7H_2O$, 0.01 g/l; $MnSO_4.4H_2O$, 0.01 g/l; $(NH_4)_2SO_4$, 50 g/l; biotin, 100 mg/l; thiamine.HCl, 1000 mg/l; soytone, 0.63 g/l; $CaCO_3$, 50 g/l; pH 7.2 adjusted with NaOH; and 10 g/l of α-amino-n-butyric acid. Lyophilized cultures obtained by the above fermentation technique have been deposited with the American Type Culture Collection as ATCC 31723. Upon analysis by high pressure liquid chromatography, fermentation broths of ATCC 31723 cultured as described above generally contain 6 mg/ml of L-isoleucine. In the absence of DL-α-amino-n-butyric-acid, the yield of L-isoleucine is greatly diminished, e.g., to about 0.2 mg/ml.

EXAMPLE 3

According to the procedure given in Example 2, the precursor used was α-ketobutyrate, (sodium salt) and the yield of L-isoleucine obtained was 6 g/l.

EXAMPLE 4

Fermentation of B. thiogenitalis ATCC No. 31723 was carried out on a medium consisting of: glucose, 10%; $(NH_4)_2SO_4$, 5%; $KH_2PO_4$, 0.30%; $MgSO_4.7H_2O$, 0.04%; $CaCO_3$, 5%; soytone, 0.3%; biotin, 100 μg/l; thiamine, 1 μ/g/l; 30 g/l of α-hydroxybutyric acid, sodium salt; and 1 ml/l of an aqueous stock solution of trace elements consisting of $ZnSO_4.7H_2O$, 8.8 g/l; $FeSO_4.7H_2O$, 10.0 g/l; $CaSO_4.5H_2O$, 0.06 g/l; $Na_2B_4O_7.10H_2O$, 0.088 g/l; $Na_2Mo_2O_4.2H_2O$, 0.053 g/l; $MnSO_4.H_2O$, 7.5 g/l; $CoCl_2.6H_2O$, 0.12 g/l; $CaCl_2$, 0.055 g/l; adjust the pH to 2.0 with $H_2SO_4$. Following admixture the pH of the "broth" was adjusted to 7.8 with NaOH.

Fifty mls. of the medium were dispensed into 250 ml. indented Erlenmeyer flasks which were inoculated and agitated at 300 rpm for 5 days at 30° C. Analysis by high pressure liquid chromatography showed that 15.8 g/l of L-isoleucine was contained in the filtered fermentation broth.

What is claimed is:

1. A process for preparing L-isoleucine which comprises cultivating under aerobic conditions a mutant strain of Brevibacterium thiogenitalis resistant to an analogue of L-isoleucine selected from the group consisting of α-amino-β-hydroxyvaleric acid; methylglycine; gammadehydroisoleucine; 3-cyclopentene-1-glycine; 2-cyclopentene-1-glycine; o-methylthreonine; and β-hydroxyleucine, said cultivation carried out in the presence of a post-threonine biosynthetic precursor of L-isoleucine selected from the group consisting of α-hydroxy butyric acid, α-aceto-α-hydroxy butyric acid, α,β-dihydroxy-β-methylvaleric acid, α-keto butyric acid, and D,L-α-amino-n-butyric acid and alkali metal salts thereof, to yield a fermentation broth, accumulating from about 0.1 to about 6 w/v percent L-isoleucine in said fermentation broth, and recovering the accumulated L-isoleucine from said fermentation broth.

2. A process as in claim 1 wherein the mutant is Brevibacterium thiogenitalis ATCC 31723.

3. A process as in claim 1 wherein the concentration of precursor in the media prior to fermentation is from 0.001 to 15 w/v percent.

4. A process as in claim 1 wherein the fermentation is carried out at a temperature of from 20° to 45° C. for from 8 to 176 hours.

5. A process as in claim 1 wherein the pH of the fermentation media during cultivation is from 5 to 9.

6. A process as in claim 1 wherein the mutant is Brevibacterium thiogenitalis ATCC 31723 and fermentation is carried out at from 20° to 45° C. for 8 to 176 hours at a pH of from 5 to 9.

7. A process as in claim 1 wherein the precursor is α-keto butyric acid or an alkali metal salt thereof.

8. A process as in claim 1 wherein the precursor is D,L-α-amino-n-butyric acid or an alkali metal salt thereof.

9. A process as in claim 1 wherein the analogue is α-amino-β-hydroxy valeric acid.

* * * * *